United States Patent [19]

Suzukamo et al.

[11] 4,182,906
[45] * Jan. 8, 1980

[54] RACEMIZATION OF OPTICALLY ACTIVE 2,2-DIMETHYL-3-(1'-ALKENYL)-CYCLOPROPANE-1-CARBOXYLIC ACIDS

[75] Inventors: Gohu Suzukamo, Ibaraki; Tsuneyuki Nagase, Takatsuki, both of Japan

[73] Assignee: Sumitomo Chemical Company, Limited, Osaka, Japan

[*] Notice: The portion of the term of this patent subsequent to Nov. 2, 1993, has been disclaimed.

[21] Appl. No.: 798,473

[22] Filed: May 19, 1977

[30] Foreign Application Priority Data

May 24, 1976 [JP] Japan .................................. 51-60288

[51] Int. Cl.² ............................................. C07C 51/00
[52] U.S. Cl. ................................. 562/506; 260/544 L; 562/401
[58] Field of Search ...................... 260/544 L, 514 H; 562/401

[56] References Cited

U.S. PATENT DOCUMENTS

| | | | |
|---|---|---|---|
| 3,794,680 | 2/1974 | Mastui | 260/514 H |
| 3,989,750 | 11/1976 | Nagase | 260/544 L |

FOREIGN PATENT DOCUMENTS 2453639  5/1975  Fed. Rep. of Germany .

*Primary Examiner*—James O. Thomas, Jr.
*Assistant Examiner*—Michael L. Shippen
*Attorney, Agent, or Firm*—Birch, Stewart, Kolasch and Birch

[57] ABSTRACT

A method for racemization of optically active 2,2-dimethyl-3-(1'-alkenyl)-cyclopropane-1-carboxylic acids of the formula:

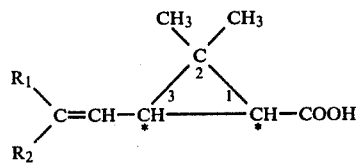

wherein $R_1$ and $R_2$ are each a hydrogen atom or an alkyl group having 1 to 4 carbon atoms or, when taken together with the carbon atom to which they are attached, represent a cycloalkylidene group having 4 to 6 carbon atoms, which comprises the step of contacting the corresponding acid halide with boron halide at a temperature of not more than 20° C.

15 Claims, No Drawings

RACEMIZATION OF OPTICALLY ACTIVE 2,2-DIMETHYL-3-(1'-ALKENYL)-CYCLOPROPANE-1-CARBOXYLIC ACIDS

The present invention relates to a method for racemization of optically active 2,2-dimethyl-3-(1'-alkenyl)-cyclopropane-1-carboxylic acids.

More particularly, it relates to a method for racemization of optically active 2,2-dimethyl-3-(1'-alkenyl)-cyclopropane-1-carboxylic acids represented by the formula:

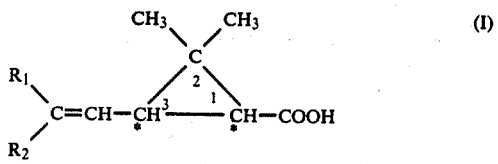

wherein $R_1$ and $R_2$ are each a hydrogen atom or an alkyl group having 1 to 4 carbon atoms or, when taken together with the carbon atom to which they are attached, represent a cycloalkylidene group having 4 to 6 carbon atoms, which comprises the step of contacting the corresponding acid halide represented by the formula:

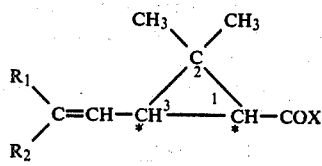

wherein X is a halogen atom and $R_1$ and $R_2$ are each as defined above with a boron halide at a temperature of not more than 20° C.

Among the cyclopropanecarboxylic acids represented by the formula (I), 2,2-dimethyl-3-(2'-methyl-1'-propenyl)-cyclopropane-1-carboxylic acid is popularly named as "chrysanthemic acid" and known to be the acid component of esters which are useful as pyrethroidal insecticides exhibiting an immediate effect with little toxicity such as pyrethrin, allethrin and phthalthrin. It is also known that esters of 2,2-dimethyl-3-vinyl-cyclopropane-1-carboxylic acid, 2,2-dimethyl-3-cyclopentylidenemethyl-cyclopropane-1-carboxylic acid, 2,2-dimethyl-3-cyclohexylidenemethyl-cyclopropane-1-carboxylic acid and the like exhibit an immediate insecticidal activity with little toxicity.

The cyclopropanecarboxylic acids (I) have four optical isomers in relation to the steric configuration at the $C_1$- and $C_3$-positions, i.e. two geometrical ones (cis form and trans form) and two optical ones ((+) form and (−) form) for each of them. Among the esters derived from these isomeric carboxylic acids, the (±) trans isomer possesses a stronger activity than the corresponding (±) cis isomer. Further, the (+) isomer exhibits a much higher effect than the corresponding (−) isomer.

In general, the cyclopropanecarboxylic acids (I) are industrially produced in the form of a racemic modification (i.e. (±) form), which comprises the cis isomer and the trans isomer. This racemic modification is then subjected to optical resolution with an optically active organic base to isolate the (+) isomer which is useful. The remaining (−) isomer, which does not have any practical value, may then be subjected to racemization and optical resolution to obtain additionally the useful (+) isomer. Thus, an efficient method for such racemization is industrially of great significance.

As shown in the above mentioned formula, the cyclopropanecarboxylic acids (I) have two asymmetric carbon atoms at the 1- and 3-positions so that racemization of them is very difficult. Epimerization at the $C_1$-position alone is comparatively easier than the racemization, and there are known several methods for such epimerization, of which examples are contacting an alkyl ester of cis-chrysanthemic acid with a specific basic catalyst under heating to obtain trans-chrysanthemic acid (U.S. Pat. No. 3,538,143), heating cis-pyrethrinic acid chloride at a high temperature (Japanese Patent Publication No. 24694/1971), etc. According to these methods, however, epimerization at both asymmetric carbon atoms can not be attained, and only the conversion of (−)-cis-chrysanthemic acid into (+)-trans-chrysanthemic acid or of (+)-cis-chrysanthemic acid into (−)-trans-chrysanthemic acid is brought about. Since these methods are based on higher thermodynamical stability of the trans isomer in comparison with the cis isomer, the conversion of the (−)-trans isomer into the (+)-trans isomer is not attained by them and may be accomplished only by changing the former to the (−)-cis isomer through complicated processes and epimerizing the resulting product at the $C_1$-position.

On the other hand, studies for realization of the racemization were made, and some procedures for the racemization have been proposed. Typical examples thereof include a method in which the alkenyl group at the $C_3$-position in (−)-trans-chrysanthemic acid is converted into a keto-alcohol group by oxidation and the carboxylic acid group at the $C_1$-position is converted into a lower alkyl ester group, which is then treated with an alkali metal alcoholate in a solvent (U.S. Pat. No. 3,282,984) and a method in which (−)-trans-chrysanthemic acid is irradiated with ultraviolet rays in the presence of a photosensitizer (U.S. Pat. No. 3,657,086). However, the former method is industrially disadvantageous because many reaction steps are required. The latter method is insufficient in the reaction efficiency and not economical, because of a large consumption of electric power for the light source.

As a result of an extensive study, it was previously found by the present inventors that the racemization of the optically active cyclopropanecarboxylic acid (I) can be attained by converting the same into its acid halide, which is then reacted with a Lewis acid as a catalyst (U.S. Pat. No. 3,989,750). In this kind of reaction, it seemed inevitable that as the reaction temperature becomes lower, the reaction time becomes longer and undesirable by-products are increased at the same time. However, it has now been found that the racemization of the optically active cyclopropanecarboxylic acid (I) can be accomplished very rapidly by treating its acid halide with a boron halide as a catalyst at a low temperature, i.e. of not more than 20° C. Advantageously, the by-products are few and the yield of the racemate is high in such a racemization. The present invention is based on the above finding.

According to the present invention, the optically active cyclopropanecarboxylic acid (I) is first converted into its acid halide by a conventional method. For example, the acid is converted into its acid chloride by treatment with a chlorinating agent such as thionyl chloride, sulfuryl chloride, oxalyl chloride, phosphoric chloride or phosphorus chloride, or into its acid bromide by treatment with a brominating agent such as phosphorus bromide. The thus obtained acid halide is then contacted with a catalytic amount a of boron halide at a temperature of not more than 20° C., usually from −70° to 20° C., whereby the racemization proceeds irrespective of the external pressure without any trouble in the reaction. The boron halide to be used as a catalyst may be boron trichloride, boron tribromide, boron trifluoride or the like. Among them, boron trichloride is particularly preferred, because it produces industrially very desirable results in the range of reaction temperature as mentioned above. In the racemization reaction, any of the four optical isomers can be used solely or in mixtures of an optical proportion as the starting material. The racemization can be attained irrespective of their optical purities.

This racemization method always gives the trans-rich reaction product regardless of the isomeric composition of the starting material. The lower that the reaction temperature obtained, the higher the percentage of the trans isomer is. Since the insecticidal activity of the esters in the trans form is generally higher than that of the corresponding esters in the cis form, the above characteristic feature of the racemization method is of great advantage. The racemization method may be also applied to the conversion of the racemic cis isomer of the acid to the corresponding racemic trans-rich isomer.

The reaction of the present invention is favorably carried out in the presence of a solvent which does neither solidify within the range of reaction temperature and nor afford any unfavorable influence on the proceeding of the racemization. Examples of the solvent include aromatic hydrocarbons or derivatives thereof (e.g. toluene, xylene, chlorobenzene), aliphatic hydrocarbons (e.g. pentane, hexane, heptane, cyclohexane) and halogen-substituted aliphatic hydrocarbons (e.g. carbon tetrachloride, chloroform, ethylene dichloride). These solvents may be used alone or in combination with each other.

The catalyst may be used in an amount of about 1/2000 to ½ mole, preferably of about 1/200 to 1/5 mole, per 1 mole of the acid halide.

The reaction of the present invention is characterized in that it proceeds very rapidly. The reaction time is associated with the amount of the catalyst and the reaction temperature. Usually, the racemization is sufficiently accomplished within a time of about 0.1 minute to 3 hours.

The racemization may be performed batchwise or continuously. The acid halide may be introduced in the whole amount from the start together with the catalyst into a reactor. If desired, it may be introduced into the reactor successively or intermittently depending upon the proceeding of the racemization.

The proceeding of the racemization can be checked by measuring the optical rotation of the reaction solution or by gas chromatography.

After completion of the reaction, the racemized acid halide can be isolated by removing the catalyst from the reaction mixture, concentrating the resulting solution and distilling the residual material as usual.

Alternatively, the reaction mixture or the racemized acid halide recovered therefrom may be treated with an aqueous alkaline solution for hydrolysis and then neutralized with a mineral acid, whereby the corresponding racemized acid can be obtained. The thus racemized product may further be converted into more favorable optically active cyclopropanecarboxylic acids by application of optical resolution.

When desired, the racemized acid halide may be, with or without its previous separation from the reaction mixture, subjected to the reaction with an alcohol which is popularly named as pyrethrolone, allethrolone or the like in the presence of a hydrogen halide-eliminating agent to obtain an ester having an insecticidal activity.

By the method of the present invention, as mentioned above in detail, the racemization of the optically active cyclopropanecarboxylic acids can be attained industrially very favorably.

Practical and presently preferred embodiments of the present invention are illustratively shown in the following Examples wherein % is by weight.

EXAMPLE 1

In a 300 ml flask, there were charged (−)-trans-2,2-dimethyl-3-isobutenylcyclopropane-1-carboxylic acid (50.0 g) and n-hexane (50 g), and thionyl chloride (41.0 g) was added thereto from a dropping funnel over a period of 30 minutes with stirring under reflux. After completion of the addition, stirring was continued for an additional 2.5 hours, and then the solvent and excess of the thionyl chloride were removed by distillation. The residue was distilled to obtain (−)-trans-2,2-dimethyl-3-isobutenylcyclopropane-1-carboxylic acid chloride (54.0 g) having a boiling point of 50° C./0.5 mmHg to 56° C./0.6 mmHg.

Other cyclopropanecarboxylic acid halides were prepared in the same manner as above.

EXAMPLE 2

In a 200 ml flask, there were charged (−)-trans-2,2-dimethyl-3-isobutenylcyclopropane-1-carboxylic acid chloride (30.0 g) and toluene (70 g). Thereafter, boron trichloride (0.94 g) was added thereto at 0° C. with stirring under a nitrogen atmosphere, and the reaction was carried out for 10 minutes. After removal of the catalyst, the toluene was recovered by distillation, and the residue was distilled to obtain racemized 2,2-dimethyl-3-isobutenylcyclopropane-1-carboxylic acid chloride (27.0 g) having a boiling point of 72°–78° C./2 mmHg. The proportion of the optical isomers in this product was determined by gas chromatography. The result was as follows: (+)-trans, 46.8%; (−)-trans, 46.7%; (+)-cis, 3.3%; (−)-cis, 3.2%.

The resulting product was hydrolyzed with an aqueous sodium hydroxide solution, followed by neutralizing and acidifying in a conventional manner. Thus, racemized 2,2-dimethyl-3-isobutenylcyclopropane-1-carboxylic acid having a melting point of 52°–54° C. was obtained.

EXAMPLES 3 to 5

In the same manner as in Example 2, the racemizations were carried out at −40° C., −20° C. and 10° C., respectively, to obtain the following results:

| Example | Reaction temperature (°C.) | Reaction time (min) | Yield of racemized acid chloride (%) |
|---|---|---|---|
| 3 | −40 | 10 | 93.0 |
| 4 | −20 | 10 | 92.5 |
| 5 | 10 | 10 | 91.0 |

EXAMPLE 6

In a 200 ml flask, there were charged (−)-trans-2,2-dimethyl-3-isobutenylcyclopropane-1-carboxylic acid (30.0 g) and toluene (70 g), and thionyl chloride (24.0 g) was added thereto from a dropping funnel at 70° to 80° C. over a period of 30 minutes with stirring. After completion of the addition, stirring was continued for an additional 2.5 hours at the same temperature. Thereafter, the reaction mixture was cooled to 0° C., and boron trichloride (0.94 g) was added thereto, followed by stirring for 30 minutes. Then, the catalyst was removed from the reaction mixture, the solvent was recovered by distillation, and the residue was distilled to obtain racemized 2,2-dimethyl-3-isobutenylcyclopropane-1-carboxylic acid chloride (28.6 g) having a boiling point of 55°–62° C./0.3 mmHg. The proportion of the optical isomers in the resulting product was determined by gas chromatography. The result was as follows: (+)-trans, 46.8%; (−)-trans, 46.8%; (+)-cis, 3.2%; (−)-cis, 3.2%.

EXAMPLE 7

In a 200 ml flask, there were charged levorotatory cis- and trans-2,2-dimethyl-3-isobutenylcyclopropane-1-carboxylic acid chloride (composition: (+)-trans, 10.6%; (−)-trans, 70.4%; (+)-cis, 4.1%; (−)-cis, 14.9%) (30 g) and carbon tetrachloride (70 g). Boron trichloride (0.95 g) was added thereto at 10° C. with stirring under a nitrogen atmosphere, and stirring was continued for 30 minutes. Then, the treatment was carried out in the same manner as in Example 2 to obtain racemized 2,2-dimethyl-3-isobutenylcyclopropane-1-carboxylic acid chloride (24.6 g). The proportion of the optical isomers in the resulting product was determined by gas chromatography. The result was as follows: (+)-trans, 46.0%; (−)-trans, 46.1%; (+)-cis, 4.0%; (−)-cis, 4.9%.

EXAMPLE 8

In a 200 ml flask, there were charged levorotatory cis- and trans-2,2-dimethyl-3-isobutenylcyclopropane-1-carboxylic acid chloride (composition: (+)-trans, 10.5%; (−)-trans, 70.5%; (+)-cis, 3.9%; (−)-cis, 15.1%) (10 g) and n-hexane (90 g). Boron trichloride (0.37 g) was added thereto at 0° C. with stirring under a nitrogen atmosphere, and stirring was continued for 2 hours. Then, the treatment was carried out in the same manner as in Example 2 to obtain racemized 2,2-dimethyl-3-isobutenylcyclopropane-1-carboxylic acid chloride (8.5 g). The proportion of the optical isomers in this product was determined by gas chromatography. The result was as follows: (+)-trans, 44.4%; (−)-trans, 48.3%; (+)-cis, 3.7%, (−)-cis, 3.6%.

EXAMPLE 9

In a 200 ml flask, there were charged levorotatory cis- and trans-2,2-dimethyl-3-isobutenylcyclopropane-1-carboxylic acid chloride (composition: (+)-trans, 14.8%; (−)-trans, 69.0%; (+)-cis, 4.1%; (−)-cis, 12.0%) (10 g) and toluene (90 g). Boron tribromide (0.9 g) was added thereto, and stirring was continued at 10° C. for 10 minutes. The proportion of the optical isomers in the resulting product was determined by gas chromatography. The result was as follows: (+)-trans, 46.1%; (−)-trans, 45.1%; (+)-cis, 4.3%; (−)-cis, 4.4%.

Then, a small amount of water was added thereto to deactivate the catalyst, and the solvent was distilled off. The residue was hydrolyzed with an aqueous sodium hydroxide solution, acidified with 20% sulfuric acid and extracted with toluene. The toluene extract was washed with water, and the solvent was removed by distillation. The residue was distilled to give racemized 2,2-dimethyl-3-isobutenylcyclopropane-1-carboxylic acid as an oily product (7.6 g) having a boiling point of 104°–110° C./0.8 mmHg, which crystallized immediately and showed a melting point of 50°–54° C.

EXAMPLE 10

In a 200 ml flask, there were charged levorotatory cis- and trans-2,2-dimethyl-3-isobutenylcyclopropane-1-carboxylic acid chloride (10.3 g) having the same composition as in Example 9 and toluene (93 g). The mixture was cooled to about −70° C., and the reaction was carried out at the same temperature with addition of a catalytic amount of boron trifluoride. After 60 minutes, a part of the reaction solution was taken out and analyzed gas-chromatographically. As the result, it was found that the acid chloride was completely racemized. Analysis of optical isomers: (+)-trans, 48.6%; (−)-trans, 48.8%; (+)-cis, 1.3%; (−)-cis, 1.3%.

EXAMPLE 11

In a 200 ml flask, there were charged (±)-cis-2,2-dimethyl-3-isobutenylcyclopropane-1-carboxylic acid chloride (30.0 g) and toluene (70 g). Thereafter, boron trichloride (0.85 g) was added thereto at 5°–10° C. with stirring under a nitrogen atmosphere, and the reaction was carried out for 10 minutes. The proportion of the isomers in the reaction mixture was determined by gas chromatography. The result was as follows: (±)-trans isomer, 91.3%; (±)-cis isomer, 8.7%.

After removal of the catalyst, the toluene was recovered by distillation, and the residue was distilled to obtain (±)-trans-rich 2,2-dimethyl-3-isobutenylcyclopropane-1-carboxylic acid chloride (27.5 g) having a boiling point of 73°–78° C./2 mmHg.

The resulting product was hydrolyzed with an aqueous sodium hydroxide solution, followed by neutralizing and acidifying in a conventional manner. Thus, (±)-trans-rich 2,2-dimethyl-3-isobutenylcyclopropane-1-carboxylic acid having a melting point of 52°–54° C. was obtained.

What is claimed is:

1. A method for the racemization of an optically active 2,2-dimethyl-3-(1'-alkenyl)-cyclopropane-1-carboxylic acid halide of the formula:

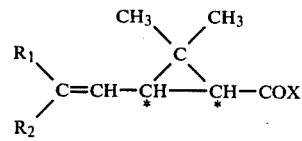

wherein $R_1$ and $R_2$ are each a hydrogen atom or an alkyl group having 1 to 4 carbon atoms or, when taken together with the carbon atom to which they are attached, represent a cycloalkylidene group having 4 to 6 carbon atoms and X is a halogen atom, which comprises contacting the acid halide with a boron halide as a catalyst at a temperature of 10° C. or less to permit the racemization to proceed until a trans-rich racemic mixture is obtained.

2. The method according to claim 1, wherein the boron halide is boron trichloride, boron tribromide or boron trifluoride.

3. The method according to claim 2, wherein the boron halide is boron trichloride.

4. The method according to claim 1, wherein the amount of the boron halide is about 1/2000 to ½ mole based on 1 mole of the acid halide.

5. The method according to claim 1, wherein the contact is effected in an inert solvent.

6. The method according to claim 5, wherein the inert solvent is an aromatic hydrocarbon or derivative thereof, an aliphatic hydrocarbon or a halogen-substituted aliphatic hydrocarbon.

7. The method according to claim 1, wherein the contact is effected at a temperature of from −70° C. to 10° C.

8. The method according to claim 1, wherein the contact is effected within a time of 0.1 minute to 3 hours.

9. The method according to claim 1, wherein the acid halide is an acid chloride.

10. A method for the conversion of the racemic cis isomer or of a mixture of the racemic cis and trans isomers of a 2,2-dimethyl-3-(1'-alkenyl)-cyclopropane-1-carboxylic acid halide of the formula:

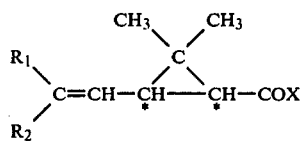

wherein $R_1$ and $R_2$ are each a hydrogen atom or an alkyl group having 1 to 4 carbon atoms or, when taken together with the carbon atom to which they are attached, represent a cycloalkylidene group having 4 to 6 carbon atoms and X is a halogen atom, into the corresponding racemic trans-rich isomer which comprises contacting the acid halide with a boron halide as a catalyst at a temperature of 10° C. or less.

11. The method of claim 10, wherein the boron halide is boron trichloride.

12. The method of claim 10, wherein the acid halide is contacted with said boron halide at a temperature of from −70° to 10° C.

13. In a method for the racemization of an optically active 2,2-dimethyl-3-(1'-alkenyl)-cyclopropane-1-carboxylic acid of the formula:

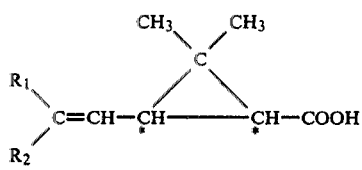

wherein $R_1$ and $R_2$ are each a hydrogen atom or an alkyl group having 1 to 4 carbon atoms or, when taken together with the carbon atom to which they are attached, represent a cycloalkylidene group having 4 to 6 carbon atoms, wherein said acid is treated with a chlorinating or brominating agent to give the corresponding acid halide, and said acid halide is racemized and hydrolyzed to the corresponding acid, the improvement which comprises contacting said acid halide with a boron halide at a temperature of 10° C. or less to permit the racemization to proceed until a trans-rich racemic mixture is obtained.

14. The method of claim 13, wherein the boron halide is boron trichloride.

15. The method of claim 13, wherein the acid halide is contacted with said boron halide at a temperature of from −70° to 10° C.

* * * * *